(12) United States Patent
Shapirov

(10) Patent No.: US 8,184,282 B2
(45) Date of Patent: May 22, 2012

(54) METHOD AND SYSTEM FOR DEFECT DETECTION USING TRANSMISSIVE BRIGHT FIELD ILLUMINATION AND TRANSMISSIVE DARK FIELD ILLUMINATION

(75) Inventor: Diana Shapirov, Yokneam (IL)

(73) Assignee: Camtek Ltd., Migdal Haemek, IL (US)

( * ) Notice: Subject to any disclaimer, the term of this patent is extended or adjusted under 35 U.S.C. 154(b) by 229 days.

(21) Appl. No.: 12/447,911

(22) PCT Filed: Nov. 1, 2007

(86) PCT No.: PCT/IL2007/001337
§ 371 (c)(1),
(2), (4) Date: Dec. 31, 2009

(87) PCT Pub. No.: WO2008/053490
PCT Pub. Date: May 8, 2008

(65) Prior Publication Data
US 2010/0110418 A1    May 6, 2010

Related U.S. Application Data

(60) Provisional application No. 60/864,004, filed on Nov. 2, 2006.

(51) Int. Cl.
*G01N 21/00* (2006.01)
(52) U.S. Cl. ................. 356/237.2; 356/237.1; 356/237.5

(58) Field of Classification Search ............... 356/237.1, 356/237.2, 237.5
See application file for complete search history.

(56) References Cited

U.S. PATENT DOCUMENTS

| | | | | |
|---|---|---|---|---|
| 5,917,588 A | * | 6/1999 | Addiego | 356/237.2 |
| 6,407,373 B1 | * | 6/2002 | Dotan | 250/201.3 |
| 6,867,424 B2 | * | 3/2005 | Kurosawa et al. | 250/559.4 |
| 7,463,350 B2 | * | 12/2008 | Nishiyama et al. | 356/237.4 |

* cited by examiner

*Primary Examiner* — Roy M Punnoose
(74) *Attorney, Agent, or Firm* — Reches Patents

(57) ABSTRACT

A method for defect detection using transmissive bright field and transmissive dark field illumination, the method includes: determining a relationship between at least one transmissive bright field illuminator (92) characteristic and at least one transmissive dark field illuminator (91) characteristic in response to at least one characteristic of each defect type out of multiple defect types that should be detected during a defect detection session and in response to at least one phenomenon to be ignored of during the defect detection session; setting the at least one transmissive bright field illuminator (92) characteristic and the at least one transmissive dark field illuminator (91) characteristic according to the determination; illuminating an at least partially transparent object by the transmissive dark field illuminator and by the transmissive bright field illuminator; detecting light that passes through the at least partially transparent object to provide detection signals, and processing the detected signals in order to detect defects.

25 Claims, 13 Drawing Sheets

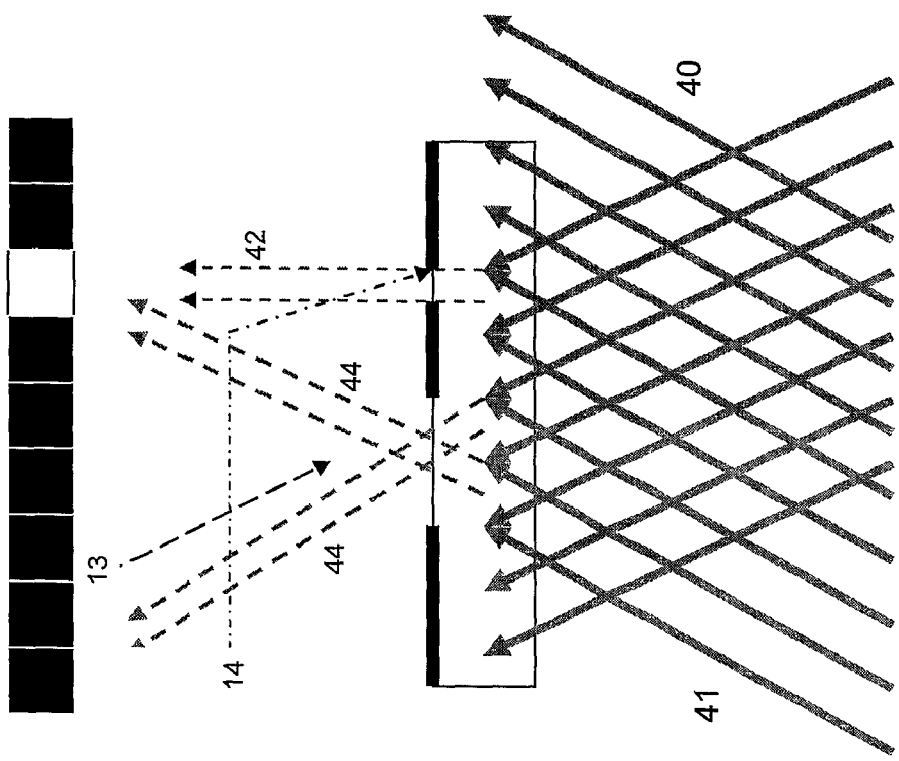
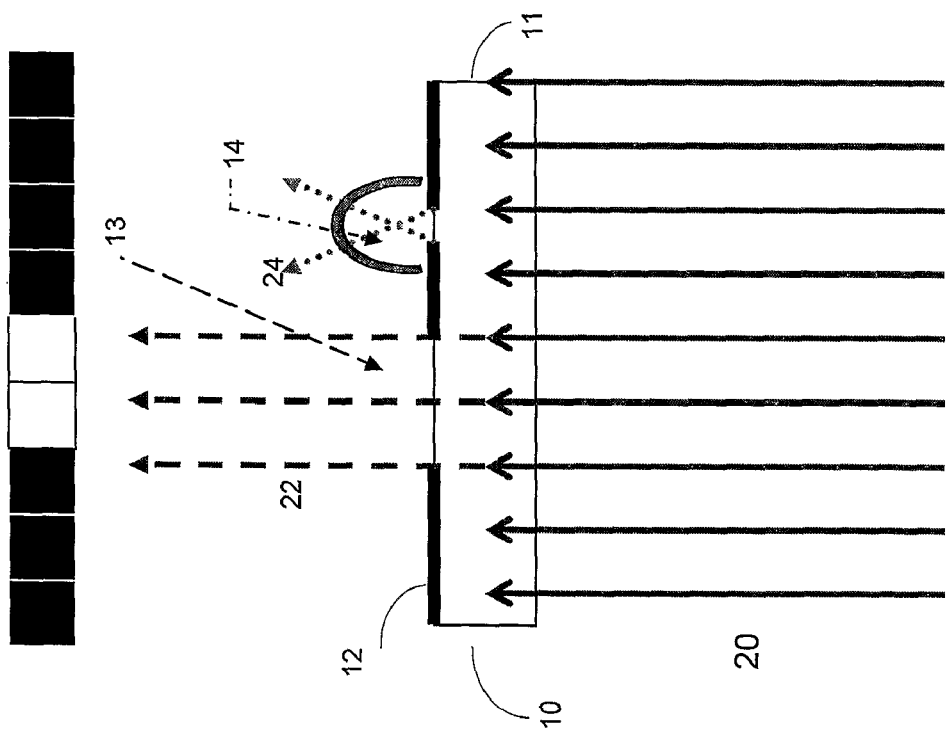
Figure 1b

Pattern

Pinhole and pattern edges pattern and small pinholes.

Small pinholes and pattern

Small pinholes and pattern

Pattern edges, coarse and fine scratches and fine pinholes

Coarse scratch and pattern

Pattern, coarse and fine scratches and fine pinholes

Contrast pattern and defects

Figure 20
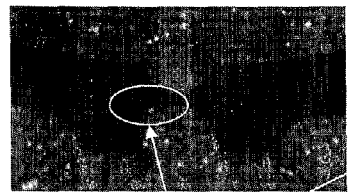
Figure 21 Pinholes Pinholes
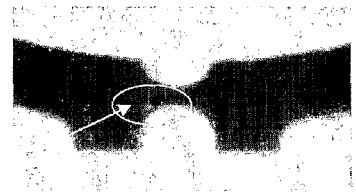
Figure 22 Pinholes
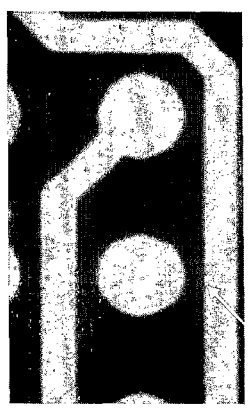
Figure 23 Scratches
Figure 24 Scratches Scratches
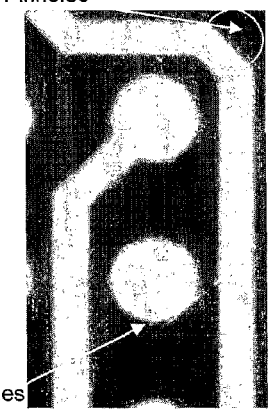
Figure 25 Scratches
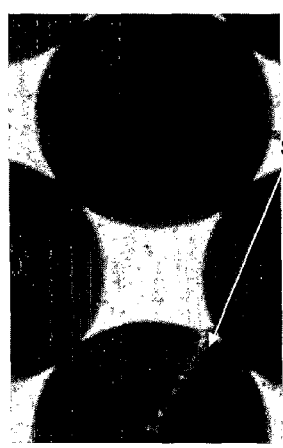
Figure 26 Scratches
Figure 27 Scratches
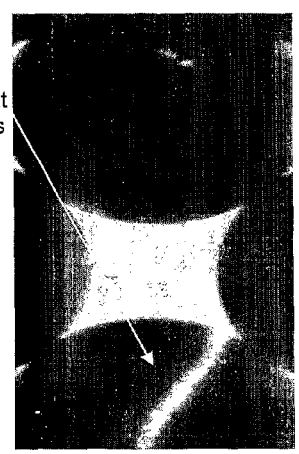
Figure 28 Scratches

```
┌─────────────────────────────────────────────────────────────────────┐
│ Processing detection signals acquired as a result of an illumination of a target by │
│ transmissive dark field illumination and by transmissive bright field illumination. The │
│ target includes defects that should be detected during the defect detection session and │
│         also includes one or more phenomena to be ignored of. 110        │
└─────────────────────────────────────────────────────────────────────┘
                                    │
┌─────────────────────────────────────────────────────────────────────┐
│ Processing detection signals acquired as a result of a simulation of an illumination of a │
│     target by transmissive dark field illumination and by transmissive bright field      │
│    illumination; wherein the target comprises defects that should be detected during the │
│    defect detection session and comprises the one or more phenomenon to be ignored of.   │
│                                    120                                                   │
└─────────────────────────────────────────────────────────────────────┘
                                    ↓
┌─────────────────────────────────────────────────────────────────────┐
│        Determining a relationship between (a) one or more transmissive bright field      │
│      illuminator characteristic and (b) one or more transmissive dark field illuminator  │
│    characteristic in response to: (i) one or more characteristics of each defect type out of │
│    multiple defect types that should be detected during a defect detection session, and (ii) │
│     one or more phenomena that should be ignored of during the defect detection session. │
│       Defect types can include large defects, small defects. medium size defects, and the │
│                                    like. 130                                             │
└─────────────────────────────────────────────────────────────────────┘
                                    ↓
┌─────────────────────────────────────────────────────────────────────┐
│   Setting the at least one transmissive bright field illuminator characteristic and the at │
│       least one transmissive dark field illuminator characteristic according to the      │
│                                 determination. 140                                       │
└─────────────────────────────────────────────────────────────────────┘
                                    ↓
┌─────────────────────────────────────────────────────────────────────┐
│       Illuminating the at least partially transparent object by the transmissive dark field │
│         illuminator and the transmissive bright field illuminator. Conveniently, this stage │
│    includes illuminating the at least partially transparent object by both transmissive dark │
│        field illuminator and transmissive bright field illuminator concurrently. 150     │
└─────────────────────────────────────────────────────────────────────┘
                                    ↓
┌─────────────────────────────────────────────────────────────────────┐
│    Detecting light that passes through the at least partially transparent object to provide │
│                              detection signals. 160                                      │
└─────────────────────────────────────────────────────────────────────┘
                                    ↓
┌─────────────────────────────────────────────────────────────────────┐
│           Processing the detected signals in order to detect defects. 170                │
└─────────────────────────────────────────────────────────────────────┘
```

100    Figure 32

```
┌─────────────────────────────────────────────────────────────────────┐
│   Processing detection signals acquired as a result of an illumination of a target by│
│ transmissive dark field illumination and by transmissive bright field illumination. The│
│  target includes defects that should be detected during the defect detection session and│
│            also includes one or more phenomena to be ignored of. 110│
└─────────────────────────────────────────────────────────────────────┘

┌─────────────────────────────────────────────────────────────────────┐
│ Processing detection signals acquired as a result of a simulation of an illumination of a│
│        target by transmissive dark field illumination and by transmissive bright field│
│   illumination; wherein the target comprises defects that should be detected during the│
│   defect detection session and comprises the one or more phenomenon to be ignored of.│
│                                    120                               │
└─────────────────────────────────────────────────────────────────────┘
                                   ↓
┌─────────────────────────────────────────────────────────────────────┐
│    Determining at least one transmissive bright field illuminator characteristic and at│
│  least one transmissive dark field illuminator characteristic so that an image of an at│
│  least partially transparent object includes pixels indicative of multiple defect types│
│       while information representative of at least one phenomenon to be ignored are│
│    substantially suppressed in the image. The image of the at least partially transparent│
│       object is obtained as a result of an illumination of the at least partially transparent│
│         object by the transmissive bright field illuminator and by the transmissive dark field│
│        illuminator. The at least partially transparent object is at least partially transparent.│
│                                    230                               │
└─────────────────────────────────────────────────────────────────────┘
                                   ↓
┌─────────────────────────────────────────────────────────────────────┐
│  Setting the at least one transmissive bright field illuminator characteristic and the at│
│         least one transmissive dark field illuminator characteristic according to the│
│                              determination. 140                      │
└─────────────────────────────────────────────────────────────────────┘
                                   ↓
┌─────────────────────────────────────────────────────────────────────┐
│      Illuminating the at least partially transparent object by the transmissive dark field│
│        illuminator and the transmissive bright field illuminator. Conveniently, this stage│
│   includes illuminating the at least partially transparent object by both transmissive dark│
│              field illuminator and transmissive bright field illuminator concurrently. 150│
└─────────────────────────────────────────────────────────────────────┘
                                   ↓
┌─────────────────────────────────────────────────────────────────────┐
│    Detecting light that passes through the at least partially transparent object to provide│
│     detection signals representative of the image of the at least partially transparent object.│
│                                    260                               │
└─────────────────────────────────────────────────────────────────────┘
                                   ↓
┌─────────────────────────────────────────────────────────────────────┐
│              Processing the detected signals in order to detect defects. 170│
└─────────────────────────────────────────────────────────────────────┘
                                   200
```

Figure 33

METHOD AND SYSTEM FOR DEFECT DETECTION USING TRANSMISSIVE BRIGHT FIELD ILLUMINATION AND TRANSMISSIVE DARK FIELD ILLUMINATION

CROSS-REFERENCE TO RELATED APPLICATIONS

This application is a National Phase Application of PCT International Application No. PCT/IL2007/001337, entitled "METHOD AND SYSTEM FOR DEFECT DETECTION USING TRANSMISSIVE BRIGHT FIELD ILLUMINATION AND TRANSMISSIVE DARK FIELD ILLUMINATION", International Filing Date Nov. 1, 2007, published on May 8, 2008 as International Publication No. WO 2008/053490, which in turn claims priority from U.S. Provisional Patent Application No. 60/864,004, filed Nov. 2, 2006, both of which are incorporated herein by reference in their entirety.

FIELD OF THE INVENTION

The invention relates to methods and systems for defect detection using transmissive dark field illumination and transmissive bright field illumination.

BACKGROUND OF THE INVENTION

During lithographic manufacturing processes masks are illuminated by ultra violet radiation in order to imprint patterns onto at least partially transparent objects. Some mask inspection tools inspect masks by using visible light. The resolution of each of the lithographic and inspection processes is inversely proportional to the wavelength of radiation using during the respective process. Accordingly, small defects (in relation to the wavelength of visible light) can be imprinted during the lithographic process while remain undetected during the mask inspection process.

For example, if small pinholes (lack of opaque material) are formed in the mask, transmissive bright field light rays that pass through the small pinholes are scattered thus causing only a non-noticeable fraction of transmissive bright field light rays to be detected by a detector. In addition, transmissive bright field illumination enhances various phenomena that are not regarded as defects (or regarded as acceptable defects that should be ignored of). These phenomena can be represented as transmissive dark spots (group of pixels that have a high gray level) on an image of the mask and can cause many false alarms. These phenomena can include background scattering centers such as dust, air bubbles, and contamination.

Accordingly, an inspection process can miss small and sub-pixel size defects, like pinholes and scratches that should be detected. In addition, pure transmissive brightfield illumination undesirably enhances various background scattering centers such as dust, air bubbles, contaminations thus causing false alarms.

FIG. 1a illustrates the problem of small pinholes invisibility. Large (diameter $d0 \gg \lambda$) and small (diameter $d1 \sim \lambda$) pinholes 2 and 2' being illuminated by uniform transmissive bright field $I_0$ (on-axis quasi plane wave) transmit strongly modulated signals $I_1$ (d0) 3 and $I_1$ (d1) 3' correspondingly. The small pinhole signal $I_1$ (d1) 3' is significantly weaker than the large one $I_1$ (d0) 3 due to diffraction effect. The additional weakening of small pinholes signal relative to those of large is provided by the diffractive limits of imaging optical system, at least partially transparent objective lens and CCD array 7. As the results the large and small pinholes gray level ratio $I_3$ (d0)/$I_3$ (d1) (as detected by CCD array 7) is too high ($\sim 10^3 \sim 10^4$) to be simultaneously visible within the same dynamic range. $I_3(d0)$ is denoted 5 while $I_3(d1)$ is denoted 5'. $I_2(d0)$ 4 represents the large pinhole signal that impinges onto CCD array 7 while $I_2(d1)$ 4' represents the small pinhole signal that impinges onto CCD array 7. It is noted that at least partially transparent objective lens 6 is positioned between the at least partially transparent object 1 (that includes pinholes 2 and 2') and CCD array 7.

The relationships between the intensities of the mentioned above signals can be calculated by the following equations:

$$\frac{I_1(d0)}{I_1(d1)} \propto \left[ \frac{J_1\left(\frac{d0}{\lambda}\right)}{J_1\left(\frac{d1}{\lambda}\right)} \cdot \frac{d1}{d0} \right]^2$$

where $J_1(x)$ is a Bessel function of the first kind of order unity and MTF are the transfer functions of the CCD and of the lens $$\frac{I_2(d0)}{I_2(d1)} \approx \frac{I_1(d0)}{I_1(d1)} \cdot \frac{MTF_{Lens}(d0)}{MTF_{Lens}(d1)}$$

$$\frac{I_3(d0)}{I_3(d1)} \approx \frac{I_2(d0)}{I_2(d1)} \cdot \frac{MTF_{CCD}\left(\frac{d0 \cdot m}{pixel\_size}\right)}{MTF_{CCD}\left(\frac{d1 \cdot m}{pixel\_size}\right)}$$

There is a growing need to provide an effective method and system for defect detection.

SUMMARY OF THE INVENTION

A method for defect detection using transmissive bright field and transmissive dark field illumination, the method includes: determining a relationship between at least one transmissive bright field illuminator characteristic and at least one transmissive dark field illuminator characteristic in response to at least one characteristic of each defect type out of multiple defect types that should be detected during a defect detection session and in response to at least one phenomenon to be ignored of during the defect detection session; setting the at least one transmissive bright field illuminator characteristic and the at least one transmissive dark field illuminator characteristic according to the determination; illuminating an at least partially transparent object by the transmissive dark field illuminator and by the transmissive bright field illuminator; detecting light that passes through the at least partially transparent object to provide detection signals; and processing the detected signals in order to detect defects.

A system for defect detection, the system includes: a transmissive dark field illuminator adapted to illuminate an at least partially transparent object that is at least partially transparent; a transmissive bright field illuminator adapted to illuminate the electrical circuit; a detector; adapted to detect light that passes through the at least partially transparent object to provide detection signals representative of an image of the electrical circuit; and a controller adapted to: (i) determine at least one transmissive bright field illuminator characteristic and at least one transmissive dark field illuminator characteristic so that the image of the at least partially transparent object comprises pixels indicative of each defect type out of multiple defect types while information representative of at least one phenomenon to be ignored while information representative of at least one phenomenon to be ignored can be filtered out; (ii) participate in setting the at least one transmissive bright field illuminator characteristic and the at least one transmissive dark field illuminator characteristic according to the determination; and (iii) process the detected signals in order to detect defects.

A method for defect detection using transmissive bright field and transmissive dark field illumination, the method includes: determining at least one transmissive bright field illuminator characteristic and at least one transmissive dark field illuminator characteristic so that an image of an at least partially transparent object comprises pixels indicative of multiple defect types while information representative of at least one phenomenon to be ignored while information representative of at least one phenomenon to be ignored can be filtered out; wherein the image of the at least partially transparent object is obtained as a result of an illumination of the at least partially transparent object by the transmissive bright field illuminator and by the transmissive dark field illuminator comprises pixels and wherein the at least partially transparent object is at least partially transparent; setting the at least one transmissive bright field illuminator characteristic and the at least one transmissive dark field illuminator characteristic according to the determination; illuminating an at least partially transparent object by the transmissive dark field illuminator and the transmissive bright field illuminator; detecting light that passes through the at least partially transparent object to provide detection signals representative of the image of the electrical circuit; and processing the detected signals in order to detect defects.

A defect detection system, the system includes: a transmissive dark field illuminator adapted to illuminate an electrical circuit; a transmissive bright field illuminator adapted to illuminate an electrical circuit; a detector; adapted to detect light that passes through the at least partially transparent object to provide detection signals; and a controller adapted to: (i) determine a relationship between at least one transmissive bright field illuminator characteristic and at least one transmissive dark field illuminator characteristic in response to at least one characteristic of each defect type out of multiple defect types that should be detected during a defect detection session and in response to at least one phenomenon to be ignored of during the defect detection session; (ii) participate in setting the at least one transmissive bright field illuminator characteristic and the at least one transmissive dark field illuminator characteristic according to the determination; and (iii) process the detected signals in order to detect defects.

BRIEF DESCRIPTION OF THE DRAWINGS

FIG. 1b illustrates transmissive bright field and transmissive dark field illumination of an at least partially transparent object according to an embodiment of the invention;

FIG. 20 illustrates a gray scale image of a sixth portion of an at least partially transparent object acquired by using transmissive bright field illumination;

FIG. 21 illustrates a gray scale image of the sixth portion of an at least partially transparent object acquired by using transmissive dark field illumination;

FIG. 22 illustrates a gray scale image of the sixth portion of an at least partially transparent object acquired by using transmissive dark field and transmissive bright field illumination according to an embodiment of the invention;

FIG. 23 illustrates a gray scale image of a seventh portion of an at least partially transparent object acquired by using transmissive bright field illumination;

FIG. 24 illustrates a gray scale image of the seventh portion of an at least partially transparent object acquired by using transmissive dark field illumination;

FIG. 25 illustrates a gray scale image of the seventh portion of an at least partially transparent object acquired by using transmissive dark field and transmissive bright field illumination according to an embodiment of the invention;

FIG. 26 illustrates a gray scale image of a eighth portion of an at least partially transparent object acquired by using transmissive bright field illumination;

FIG. 27 illustrates a gray scale image of the eighth portion of an at least partially transparent object acquired by using transmissive dark field illumination;

FIG. 28 illustrates a gray scale image of the eighth portion of an at least partially transparent object acquired by using transmissive dark field and transmissive bright field illumination according to an embodiment of the invention;

FIGS. 32 and 33 illustrate methods for combining transmissive dark field and transmissive bright field illumination for defect detection according to various embodiments of the invention.

DETAILED DESCRIPTION OF THE DRAWINGS

The phrase "at least partially transparent object" means an at least partially transparent object at least partially transparent object that includes at least one transparent portion and can also include at least one opaque portion. The at least partially transparent object can be a lithography mask or a printed circuit board but this is not necessarily so.

The phrase "defect detection session" means one or more operations that can assist in detecting defects. A defect detection session can include finding defects in one or more portions of an electrical circuit, in one or more electrical circuits, may involve processing one or more images of one or more portions of an at least partially transparent object and the like. It is noted that multiple defect detection sessions can be applied in order to find defects in a single portion of an electrical circuit.

The term "pinhole" means an absence of opaque material. It can have a circular shape but this is not necessarily so. A pinhole can be delimited by an opaque pattern. A fine (small) pinhole is small in relation to the wavelength of a radiation used during a defect detection session.

According to an embodiment of the invention a transmissive bright field transmissive illuminator and a transmissive dark field transmissive illuminator are used to illuminate an at least partially transparent object that is at least partially transparent. The transmissive dark field transmissive illuminator and transmissive bright field transmissive illuminator are tuned such as to cause defects of multiple types to be detected and to reduce false alarms resulting from one or more phenomena to be ignored of.

Conveniently, the relative intensities and, additionally or alternatively, the angular relationships between transmissive dark field light beans and transmissive bright field light beams are determined in order to enable a detection of small (fine) and large (coarse) defects while preventing false alarms generated by one or more phenomena such as air bubbles, dust and contamination.

Figure 1A:
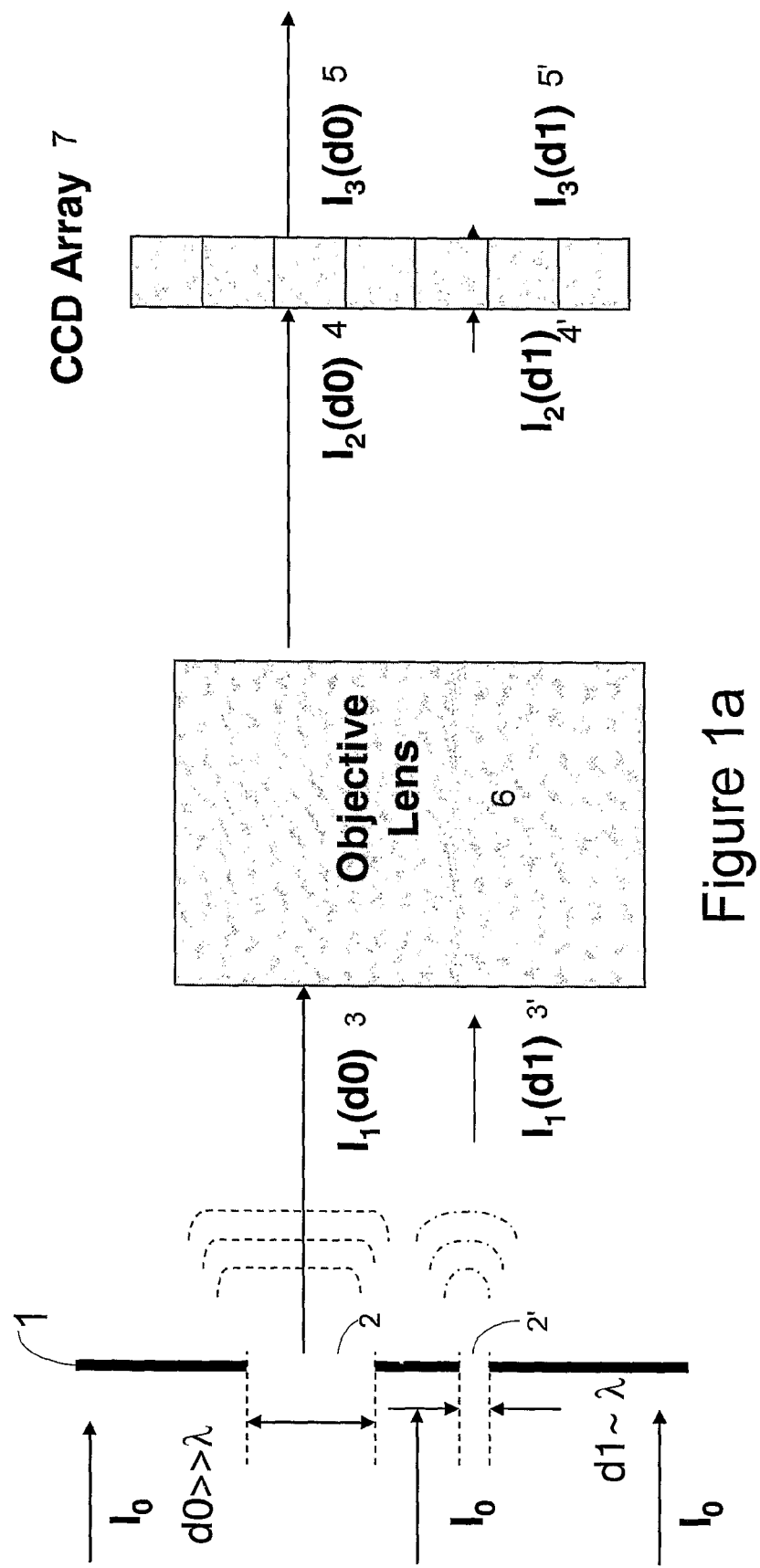
FIG. 1a illustrates a transmissive bright field illumination of an at least partially transparent object.
Figure 1C:
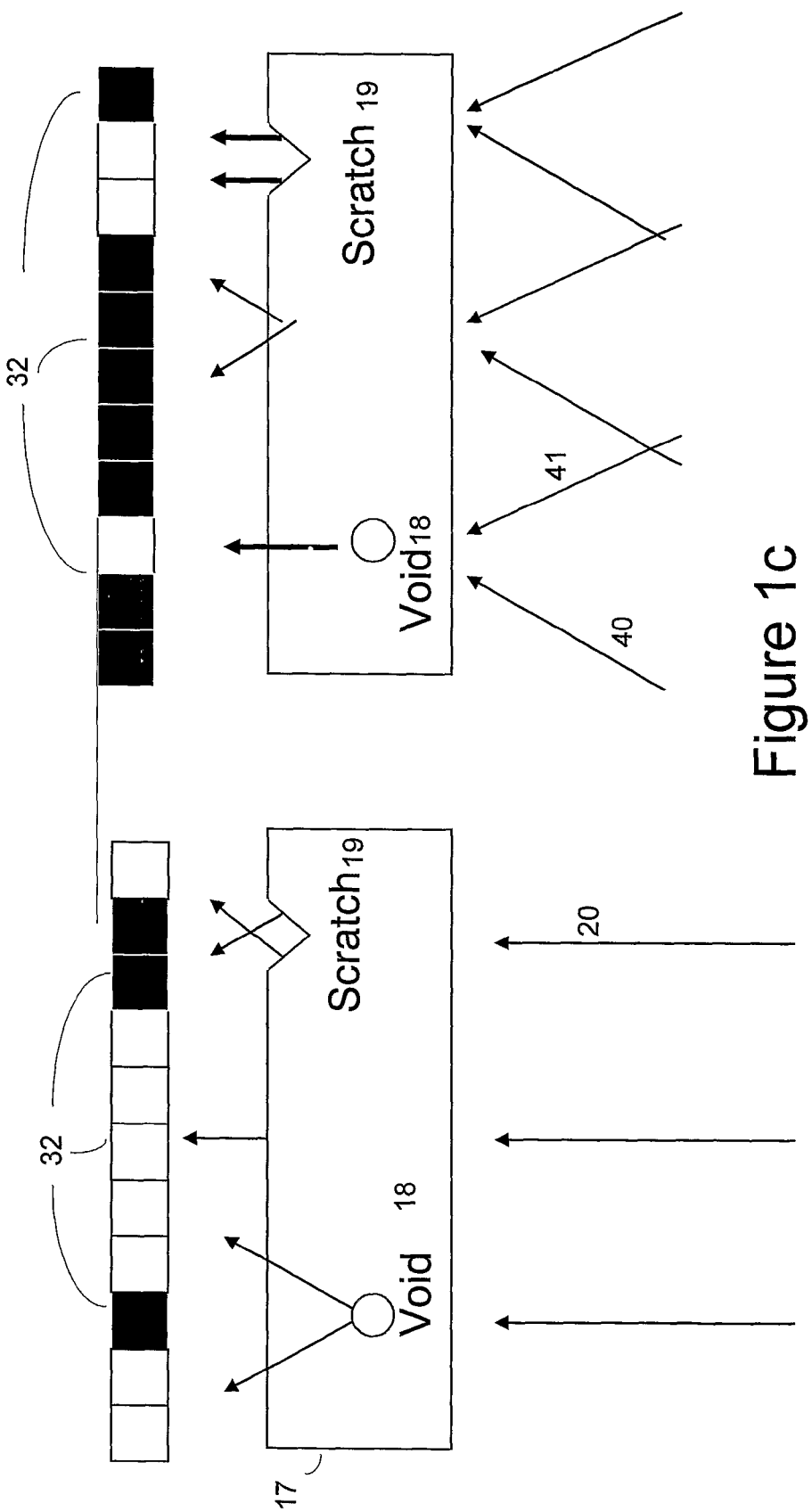
FIG. 1c transmissive illustrates transmissive bright field and transmissive dark field illumination of an at least partially transparent object according to an embodiment of the invention.
Figure 2:
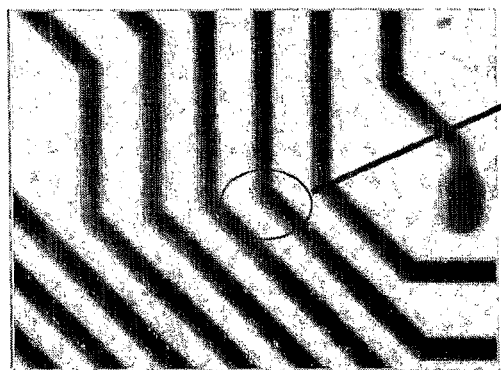
FIG. 2 illustrates a gray scale image of a first portion of an at least partially transparent object acquired by using transmissive bright field illumination.
Figure 3:
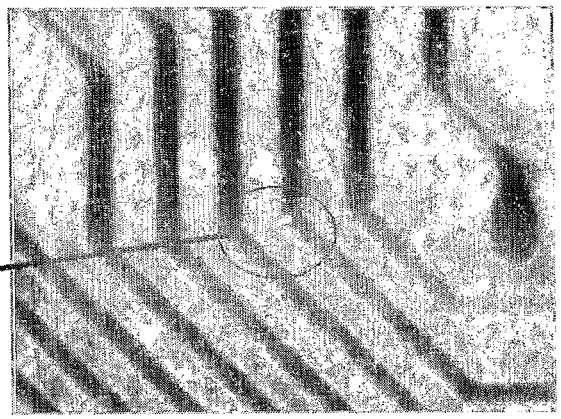
FIG. 3 illustrates a gray scale image of the first portion of an at least partially transparent object acquired by using transmissive dark field illumination.
Figure 4:
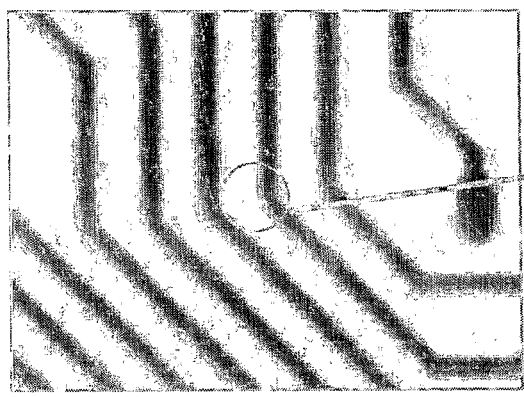
FIG. 4 illustrates a gray scale image of the first portion of an at least partially transparent object acquired by using transmissive dark field and transmissive bright field illumination according to an embodiment of the invention.
Figure 5:
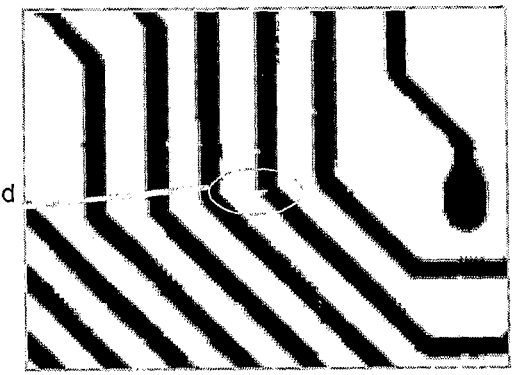
FIGS. 5 and 6 illustrate binary images obtained after binarizing the gray scale image of FIG. 4 according to an embodiment of the invention.
Figure 6:
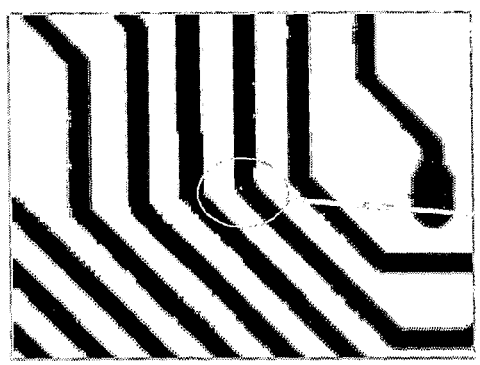
Figure 7:
FIG. 7 illustrates a gray scale image of a second portion of an at least partially transparent object acquired by using transmissive bright field illumination.
Figure 8:
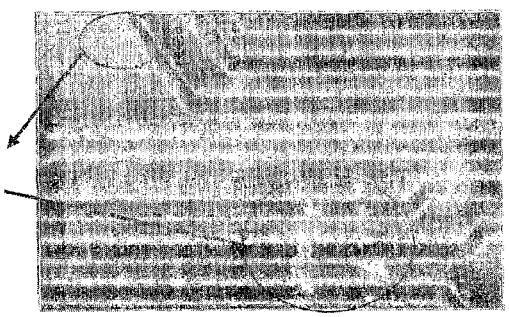
FIG. 8 illustrates a gray scale image of the second portion of an at least partially transparent object acquired by using transmissive dark field illumination.
Figure 9:
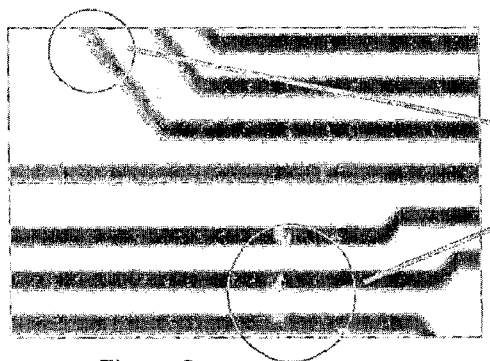
FIG. 9 illustrates a gray scale image of the second portion of an at least partially transparent object acquired by using transmissive dark field and transmissive bright field illumination according to an embodiment of the invention.
Figure 10:
FIG. 10 illustrates a binary image obtained after binarizing the gray scale image of FIG. 9 according to an embodiment of the invention.
Figure 11:
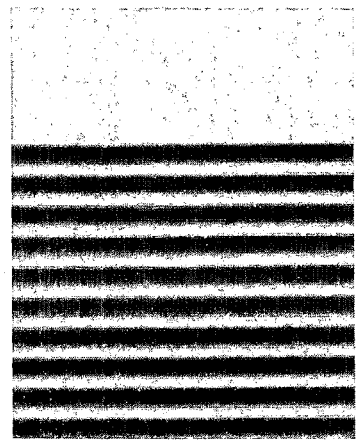
FIG. 11 illustrates a gray scale image of a third portion of an at least partially transparent object acquired by using transmissive bright field illumination.
Figure 12:
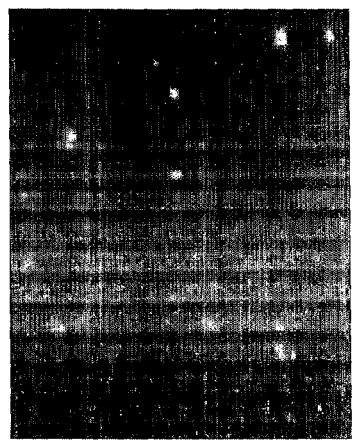
FIG. 12 illustrates a gray scale image of the third portion of an at least partially transparent object acquired by using transmissive dark field illumination.
Figure 13:
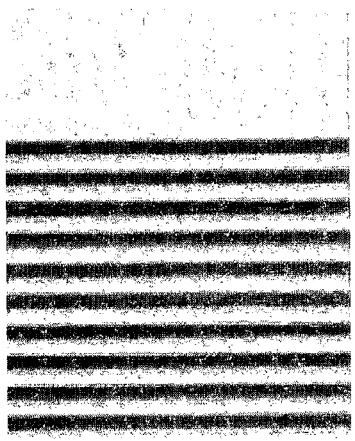
FIG. 13 illustrates a gray scale image of the third portion of an at least partially transparent object acquired by using transmissive dark field and transmissive bright field illumination according to an embodiment of the invention.
Figure 14:
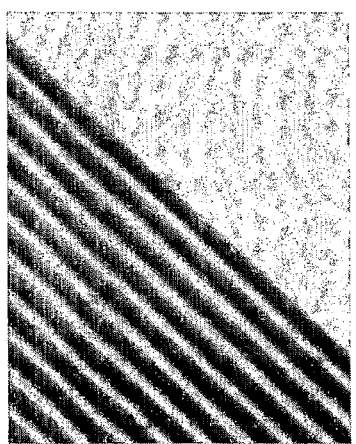
FIG. 14 illustrates a gray scale image of a fourth portion of an at least partially transparent object acquired by using transmissive bright field illumination.
Figure 15:
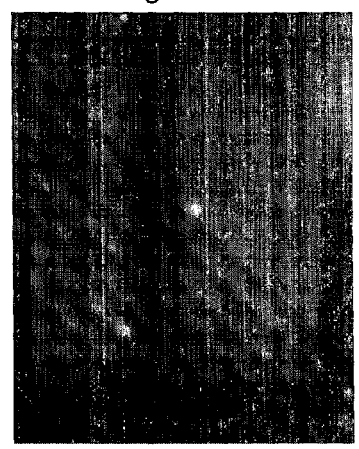
FIG. 15 illustrates a gray scale image of the fourth portion of an at least partially transparent object acquired by using transmissive dark field illumination.
Figure 16:
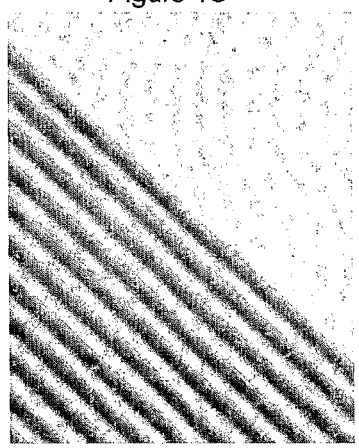
FIG. 16 illustrates a gray scale image of the fourth portion of an at least partially transparent object acquired by using transmissive dark field and transmissive bright field illumination according to an embodiment of the invention.
Figure 17:
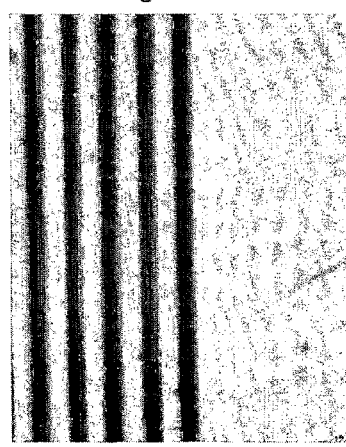
FIG. 17 illustrates a gray scale image of a fifth portion of an at least partially transparent object acquired by using transmissive bright field illumination.
Figure 18:
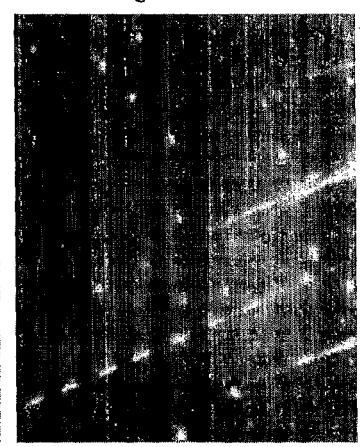
FIG. 18 illustrates a gray scale image of the fifth portion of an at least partially transparent object acquired by using transmissive dark field illumination.
Figure 19:
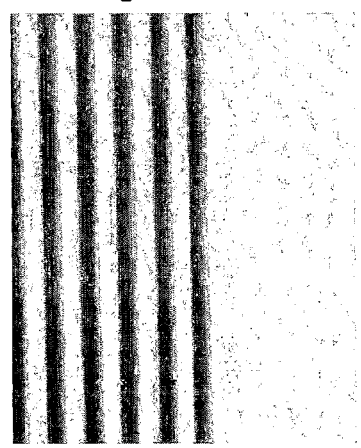
FIG. 19 illustrates a gray scale image of the fifth portion of an at least partially transparent object acquired by using transmissive dark field and transmissive bright field illumination according to an embodiment of the invention.

FIGS. 1a-1c illustrate illumination paths FIGS. 2-28 illustrate various images acquired by applying transmissive dark field illumination, transmissive bright field illumination or a combination thereof.

Various images of portions of at least partially transparent object portions are shown in FIGS. 6-28. These portions includes opaque patterns that are positioned above (or below) a transparent layer. Transmissive bright field illumination (also referred to as on axis illumination) includes illuminating these electrical circuits by transmissive bright field light beams that are perpendicular to the electrical circuits, which they have to pass through. Transmissive dark field illumination (also referred to as off axis illumination) includes illuminating these at least partially transparent object portions by transmissive dark field light beams that are oriented in respect to the normal of these at least partially transparent object portions. An imaging module includes a detector that includes a sensor array (such as a CCD array) that has a sensing surface. The sensing surface is substantially parallel to the at least partially transparent object portions. Conveniently, the electrical circuits are masks that include a glass or polymer layer on which opaque (chrome or emulsion) patterns are formed.

Referring to FIG. 1b, portion 10 of an at least partially transparent object includes a transparent layer 11 and an opaque pattern 12 that defined a large (coarse) pinhole 13 and a small (fine) pinhole 14. When illuminating at least partially transparent object 10 with transmissive bright field light rays 20 some light rays pass through the large pinhole 13 to be detected by a detector array while transmissive bright field light rays that enter small pinhole 14 are scattered over a large angular range such as not to affect the transmissive bright field image 30 of at least partially transparent object 10. It is assumed that light rays that are not substantially perpendicular to the sensing surface of the detector are not detected by the detector. When illuminating at least partially transparent object 10 with transmissive dark field light rays 40 and 41 some transmissive dark field light rays 44 pass through the large pinhole 13 are not perpendicular to the sensor array and are not detected. Some transmissive dark field light rays 42 enter small pinhole 14 are scattered in a normal direction to at least partially transparent object 10 and are detected by a detector such as to affect the transmissive dark field image 31 of the electrical circuit.

During a defect detection session a so-called optical image of the at least partially transparent object portion is projected onto the sensor array. This optical image is represented by a gray level image that includes multiple detection signals. The gray level image can be Binarized to provide a binary image.

The gray level image of the at least partially transparent object portion obtained by using only transmissive bright field illumination can include pattern, large defects and phenomena such as dust, air bubbles, scratches or contamination. The binary image that is obtained using only transmissive bright field illumination can include black pixels on a white background that represent the pattern and especially relatively large defects such as large pinholes. Black pixels on a white background can also represent phenomena such as dust, air bubbles, scratches or contamination that attenuate the light that passes through these phenomena so that the received light intensity is below the binarization threshold. These black pixels can cause many false alarms.

The gray level image of the at least partially transparent object obtained by using only transmissive dark field illumination can include pattern edges, small defects and phenomena such as dust, air bubbles, scratches or contamination. The binary image that is obtained using only transmissive dark field illumination can include white pixels on a black background that represent pattern edges and relatively small defects that scatter off-axis transmissive dark field light rays at a direction that is substantially parallel to the normal of the electrical circuit. White pixels on a black background can also represent phenomena such as dust, air bubbles, scratches or contamination.

By setting the transmissive dark field and transmissive bright field transmissive illuminators such as to compensate for difference in the acquisition of transmissive bright field and transmissive dark field illumination a hybrid gray level image of the at least partially transparent object is obtained.

Typically, the light intensity of the transmissive dark field illuminator is higher than the intensity of the transmissive bright field illuminator thus virtually amplifying the transmissive dark field component of each hybrid image pixel.

Accordingly, amplified transmissive dark field components of pixels representative of phenomenon such as dust, air bubbles and contamination cause these pixels to exceed the binarization threshold and appear as white pixels in the binary image. A defect detection analysis can easily ignore these white pixels, especially when these pixels are not located within regions that are expected to include black pattern pixels.

Accordingly, amplified transmissive dark field components of pixels representative of small defects exceed the binarization threshold and appear as white pixels. A defect detection analysis can easily define these white pixels as defects when these white pixels appear in locations that are expected to include pattern pixels.

Accordingly, FIG. 1b illustrates that transmissive bright field illumination 20 can serve to visualizes just regular pattern (macro-at least partially transparent objects) while the small defects (various macro-at least partially transparent objects like pinholes, scratches and nicks) do not affect transmissive bright field image 30 due to diffractive effects (as illustrated in FIG. 1a). The oblique beams 40 and 41 from transmissive dark field illumination 40 and 41 that pass through the regular pattern without declination and are not detected in transmissive dark field image 31. On the other hand, the oblique beams 40 and 41 pass through small pinhole 14 they are declined into the CCD array direction due to the same diffraction effect. Transmissive bright field and transmissive dark field illuminations create two complimentary images (30 and 31) for the same work-piece. The transmissive bright field image 30 includes information about regular pattern and the transmissive dark field image 31 provides information about small defects. Both images form a hybrid image. The transmissive bright field image transmissive brightness is proportional to the applied illumination and detector (CCD array) response. The transmissive dark field image transmissive brightness, i.e., the strength of signal formed by small defect in CCD array, depends on much more factors: applied illumination power, angular distribution and spectrum, defect size and form, numerical imaging optics aperture. The optimal combination of transmissive bright field and transmissive dark field illumination should be predefined and controllable for equalizing macro-at least partially transparent objects (such as patterns) and micro-at least partially transparent objects (such as small pinholes) signals strength.

FIG. 1c illustrates how a combination of transmissive bright field and transmissive dark field illumination reduced false alarms that can be caused by solely using transmissive bright field illumination. Various defects, such as scratch 19 and void 18 (but also bubbles and dust that are not shown) located within non-masked regions of a transparent substrate 17 should not appear as defects. As scattering centers those defects appear "black" on "white" under transmissive bright field illumination (see transmissive bright field image 32), and, vice versa, "white" on "black" under transmissive dark field illumination (see transmissive dark field image 33). The proper combination of transmissive bright and transmissive dark field illumination eliminates them from a hybrid image that includes both transmissive bright and transmissive dark field images. Accordingly the false alarms are greatly reduced.

Figure 29:
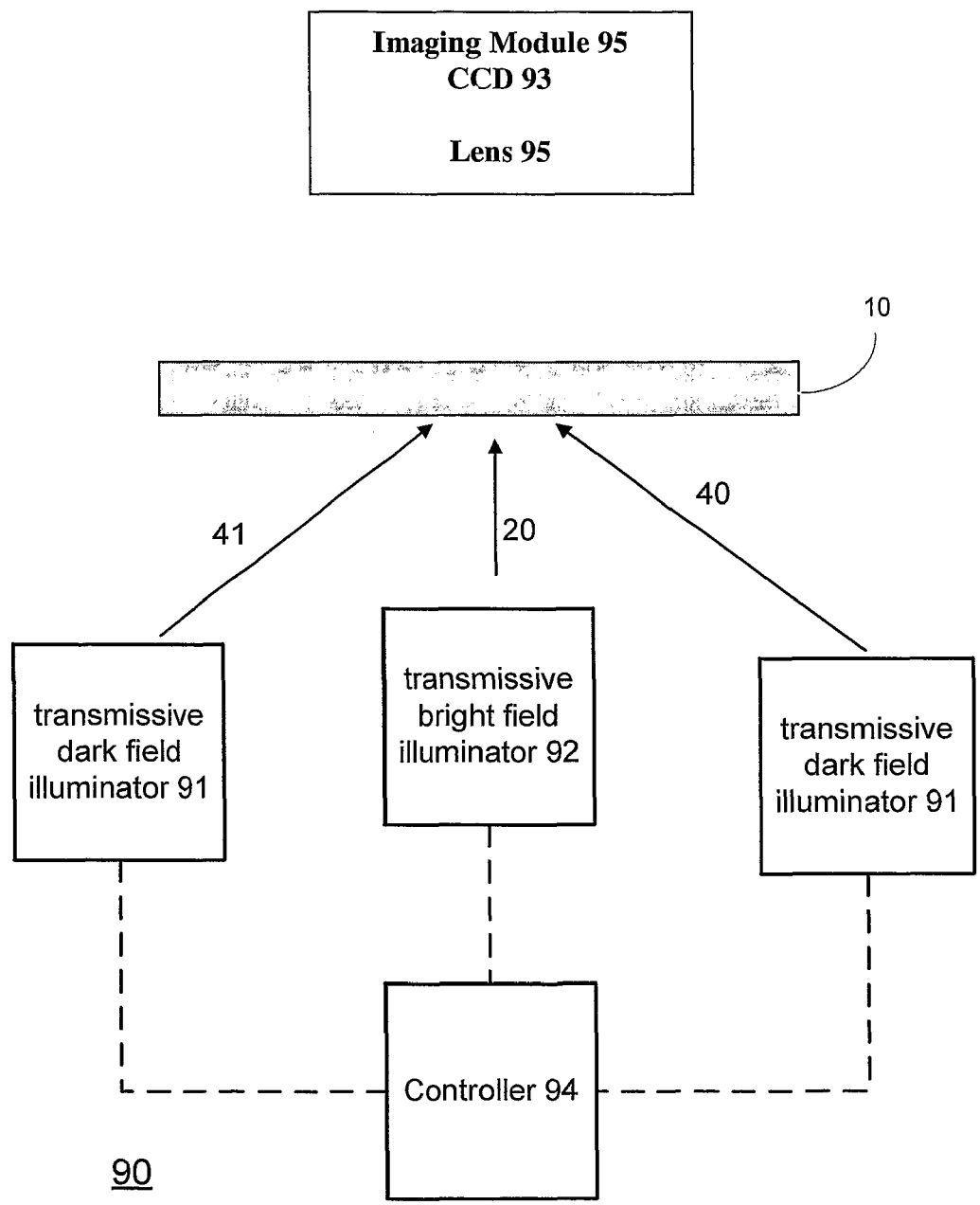
FIGS. 29-30 illustrate a device and various portions of the device according to various embodiments of the invention.

FIG. 29 illustrates defect system 90 according to an embodiment of the invention. Defect detection system 90 includes: transmissive dark field illuminator 91 that is adapted to illuminate an electrical circuit, transmissive bright field illuminator 92 adapted to illuminate an electrical circuit; detector 93 (such as a sensor array) that is adapted to detect light that passes through the at least partially transparent object to provide detection signals; and controller 94 that is adapted to: (i) determine a relationship between at least one transmissive bright field illuminator characteristic and at least one transmissive dark field illuminator characteristic in response to at least one characteristic of each defect type out of multiple defect types that should be detected during a defect detection session and in response to at least one phenomenon to be ignored of during the defect detection session; (ii) participate in setting the at least one transmissive bright field illuminator characteristic and the at least one transmissive dark field illuminator characteristic according to the determination; and (iii) process the detected signals in order to detect defects. It is noted that typically one at least partially transparent object portion is illuminated at a time; alternatively the entire at least partially transparent object can be illuminated at a time.

Detector 93 is included within imaging optics 95. Imaging optics also includes one or more lenses 96 that image a certain plane (for example bottom surface or upper surface) of at least partially transparent object 10 onto detector 93.

According to another embodiment of the invention detector 93 is adapted to detect light that passes through the at least partially transparent object to provide detection signals representative of an image of the at least partially transparent object and controller 94 is adapted to: (i) determine at least one transmissive bright field illuminator characteristic and at least one transmissive dark field illuminator characteristic so that the image of the at least partially transparent object comprises pixels indicative of each defect type out of multiple defect types while information representative of at least one phenomenon to be ignored can be filtered out; (ii) participate in setting the at least one transmissive bright field illuminator characteristic and the at least one transmissive dark field illuminator characteristic according to the determination; and (iii) process the detected signals in order to detect defects.

For simplicity of explanation other components were not illustrated. These components can include, for example, a memory unit for storing image information, power supply, at least partially transparent object loading mechanism and an at least partially transparent object stage that supports and can optionally move the electrical circuit.

It is noted that controller 94 can control the operation of various components of defect detection system 90 and also has image processing capabilities. Those of skill in the art will appreciate that the controlling modules of controller 94 can be separated from the image processing modules of controller 94. Controller 94 has many components that can be arranged in a distributed manner, a centralized manner or a combination thereof.

Defect detection system 90 can apply either one of method 100 and 200 of FIGS. 32 and 33.

Figure 30:
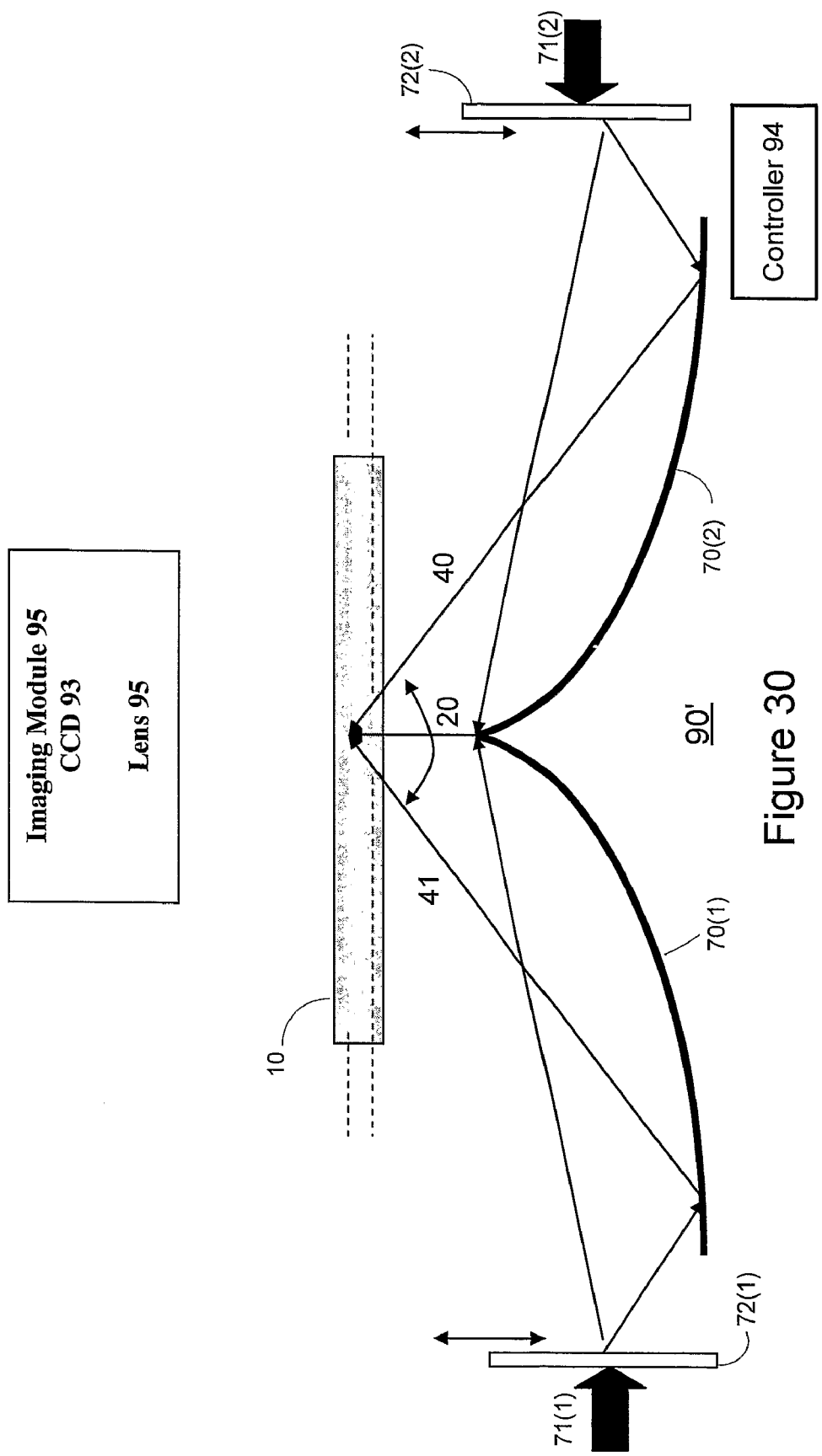

FIG. 30 illustrates defect system 90' according to an embodiment of the invention. Defect detection system 90 includes: controller 94 such as controller 94 of FIG. 29, elliptical mirrors 70(1) and 70(2); light sources 71(1) and 71(2) and movable transmissive deflectors 72(1) and 72(2). Such an optical arrangement is illustrated in PCT patent application serial number PCT/IL2006/000951 which is incorporated herein by reference.

Light source 70(1) illuminates movable transmissive deflector 72(1). The illuminated light passes through movable transmissive deflector 72(1) and impinges onto elliptical mirror 70(1). The elliptical mirror 70(1) reflects the light towards at least partially transparent object 10 to provide transmissive dark field light beam 41 and a portion of transmissive bright field light beam 20.

Light source 70(2) illuminates movable transmissive deflector 72(2). The illuminated light passes through movable transmissive deflector 72(2) and impinges onto elliptical mirror 70(2). The elliptical mirror 70(2) reflects the light towards at least partially transparent object 10 to provide transmissive dark field light beam 40 and another portion of transmissive bright field light beam 20.

The movable transmissive deflectors 72(1) and 72(2) can be moved along a virtual vertical axis. The angular relationship between each movable transmissive deflector (72(1), 72(2)) and its corresponding light source (70(1), 70(2)) determines the angle of transmissive dark field light beams 41 and 40. Controller 94 can: (i) determine the required relationships between these intensities and the angular location of the movable transmissive deflectors in response to at least one characteristic of each defect type out of multiple defect types that should be detected during a defect detection session and in response to at least one phenomenon to be ignored of during the defect detection session; (ii) participate in setting these intensities and the angular location according to the determination; and (iii) process the detected signals in order to detect defects. It is noted that typically one at least partially transparent object portion is illuminated at a time; alternatively the entire at least partially transparent object can be illuminated at a time.

Figure 31A:
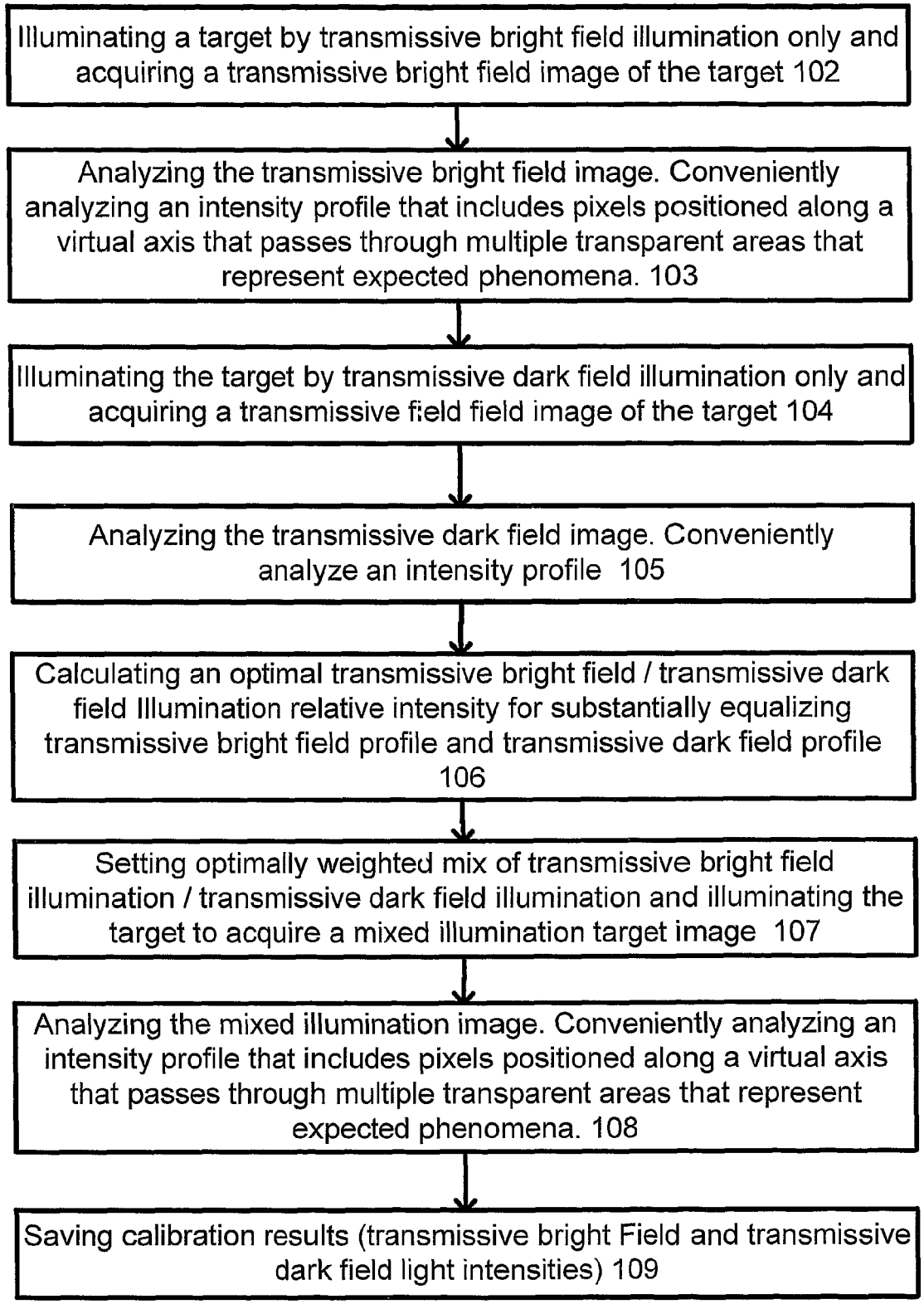
FIG. 31a illustrates a calibration sequence and according to an embodiment of the invention.
Figure 31B:
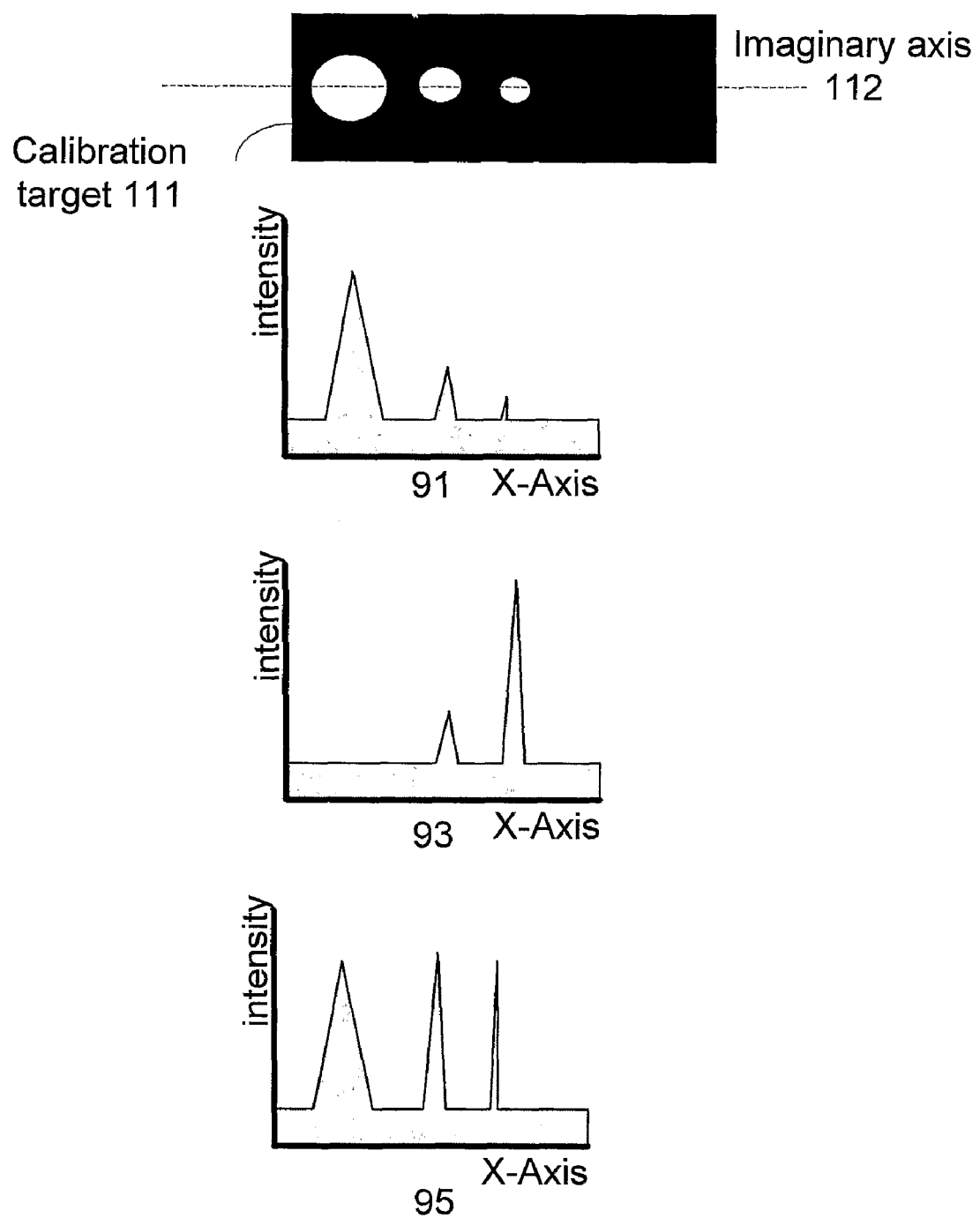
FIG. 31b illustrates a calibration target and some intensity profiles according to an embodiment of the invention.

FIG. 31*a* illustrates a calibration phase according to an embodiment of the invention. FIG. 31*b* illustrates a calibration target 111 and intensity profiles 91, 93 and 95 according to various embodiments of the invention.

Calibration phase 101 includes stage 102-109. Stage 102 includes illuminating a target by transmissive bright field illumination only and acquiring a transmissive bright field image of the target. Stage 103 includes analyzing the transmissive bright field image. Conveniently analyzing an intensity profile (such as profile 91 of FIG. 31*b*) that includes pixels positioned along a virtual axis that passes through multiple transparent areas that represent expected phenomena. Stage 104 includes illuminating the target by transmissive dark field illumination only and acquiring a transmissive dark field image of the target. Stage 105 includes analyzing the transmissive dark field image. Conveniently analyze an intensity profile such as profile 95 of FIG. 31*b*. Stage 105 can be followed by stage 110 of FIG. 32. According to an embodiment of the invention stage 110 includes stage 106 of calculating an optimal transmissive bright field/transmissive dark field Illumination relative intensity for substantially equalizing transmissive bright field profile and transmissive dark field profile. Stage 107 includes setting optimally weighted mix of transmissive bright field illumination/transmissive dark field illumination and illuminating the target to acquire a mixed illumination target image. Stage 108 includes analyzing the mixed illumination image. Conveniently analyzing an intensity profile (such as profile 95 of FIG. 31*c*) that includes pixels positioned along a virtual axis that passes through multiple transparent areas that represent expected phenomena. As illustrated in FIG. 31*b*, the optimal mixed profile includes dark field and bright field peaks of the same intensity. It is noted that other optimization schemes can be applied. Stage 109 includes saving calibration results (transmissive bright Field and transmissive dark field light intensities). These results are used to set the transmissive bright field illuminator and the transmissive bright field illuminator.

The calibration phase can starts by stage 101 of setting full Illumination (transmissive bright and transmissive dark) and acquiring a target image for calibration objects position identification and alignment 101. The target can include multiple irregularities (such as pinholes, scratches, and the like). A sample target 111 is illustrated in FIG. 35.

FIG. 32 illustrates method 100 for defect detection using transmissive bright field illumination and transmissive dark field illumination according to an embodiment of the invention.

Method 100 starts by either one of stages 110 or 120. During these stages method 100 tries to evaluate how defects of different types will be detected based upon an actual or a simulated illumination of a target by a transmissive dark field illuminator and a transmissive bright field illuminator. Stage 110 and 120 can be viewed as a calibration phase of method 100. It is noted that multiple repetitions of this calibration phase can occur wherein the settings of the transmissive bright field and transmissive dark field illuminators can differ from one iteration to another. FIG. 31 illustrates in greater details a target and a calibration phase.

Stage 110 includes processing detection signals acquired as a result of an illumination of a target by transmissive dark field illumination and by transmissive bright field illumination. The target includes defects that should be detected during the defect detection session and also includes one or more phenomena to be ignored of. Conveniently stage 110 includes illuminating the target with the transmissive bright field illuminator and the transmissive dark field illuminator, obtaining detection signals, changing the setting (changing one or more characteristic) of either one of the transmissive bright field illuminator and the transmissive dark field illuminator and repeating the illuminating, obtaining of detection signals and changing the setting.

The maximal number of iterations can be limited, and, additionally or alternatively, can be dependent upon the results of the illuminations. Thus, the repetitions can stop once defects of different types appear in an image of the target at least partially transparent object while one or more phenomenon either do not appear in the image or appear in a manner that slightly affects the detection process.

For example, if pixels that represent the one or more phenomenon can be easily filtered out then they can be regarded as slightly affecting the detection process. The same can be said about pixels of a phenomenon that have substantially the same intensity as pixels of their phenomenon-free surroundings.

Stage 120 includes processing detection signals acquired as a result of a simulation of an illumination of a target at least partially transparent object by transmissive dark field illumination and by transmissive bright field illumination; wherein the target at least partially transparent object comprises defects that should be detected during the defect detection session and comprises the one or more phenomenon to be ignored of.

Stages 110 and 120 are followed by stage 130 of determining a relationship between (a) one or more transmissive bright field illuminator characteristic and (b) one or more transmissive dark field illuminator characteristic in response to: (i) one or more characteristics of each defect type out of multiple defect types that should be detected during a defect detection session, and (ii) one or more phenomena that should be ignored of during the defect detection session. Defect types can include large defects, small defects. medium size defects and the like. A defect characteristic can indicate how the defect is captured by the sensor array. This can include whether or not such a defect is captured as well as the expected intensity of light that will reach the sensor array as a result of the defect. For example, a small pinhole will not be captured by using merely transmissive bright field illumination but can be captured by using transmissive dark field illumination. Although the intensity of light that is captured by the sensor array (as a result of the small defect) will be relatively low.

Stage 130 should compensate for differences in the light intensity that can be collected by a detector as a result of applying transmissive dark field illumination and transmissive bright field illumination. Referring to the example set fourth in FIG. 1, the intensity of light that passes through a large hole in an at least partially transparent object (when the at least partially transparent object is illuminated by a transmissive bright field illuminator) exceeds the intensity of light that passes through a small hole in the at least partially transparent object (when the at least partially transparent object is illuminated by a transmissive dark field illuminator).

Stage 130 can include determining the relationship between one or more of the following: (i) the intensities of the transmissive dark field and transmissive bright field illuminators, (ii) the optical axis of the transmissive bright field illuminator and the transmissive dark field illuminator; (iii) the radiation pattern (shape of cross section, beam width) of the transmissive bright field illuminator and the radiation pattern of the transmissive dark field illuminator.

Conveniently, stage 130 include determining the relationship between one or more transmissive bright field illuminator characteristic and one or more transmissive dark field illuminator characteristic so that intensities of detection signals obtained as a result of an illumination (by the transmissive dark field illuminator and by the transmissive bright field illuminator) of expected defects of different types are within a narrow range that is substantially narrower than the dynamic range of a detector that generates the detection signals. This narrow range can be defined, for example, by the binarization threshold.

Conveniently, the intensity of pixels that represent defects of different sizes (small defects, large defects) should be within a narrow range that is much smaller than the dynamic range of the detector. Conveniently, the intensity of such pixels is substantially indifferent to the size of the defect. Conveniently, the relationship is determined so that intensities of detection signals obtained as a result of an illumination, by the transmissive dark field illuminator and by the transmissive bright field illuminator, of expected defects of different types are substantially the same.

Conveniently, stage 130 includes determining the relationship between the one or more characteristic of the transmissive dark field illuminator and the one or more characteristic of the transmissive bright field illuminator so that that an image of the at least partially transparent object comprises pixels representative of small defects of the at least partially transparent object and pixels representative of large detects of the at least partially transparent object and wherein pixels representative of air bubbles, dust or contamination have values that indicate that these are not defects.

Stage 130 is followed by stage 140 of setting the at least one transmissive bright field illuminator characteristic and the at least one transmissive dark field illuminator characteristic according to the determination.

Stage 140 is followed by stage 150 of illuminating the at least partially transparent object by the transmissive dark field illuminator and the transmissive bright field illuminator. Conveniently, this stage includes illuminating the at least partially transparent object by both transmissive dark field illuminator and transmissive bright field illuminator concurrently. The illumination can include pulsed illumination or continuous illumination.

Stage 150 is followed by stage 160 of detecting light that passes through the at least partially transparent object to provide detection signals.

Stage 160 is followed by stage 170 of processing the detected signals in order to detect defects. The processing can include binarizing a gray level image to provide a binary image. It is further noted that stage 170 can also include processing gray level images without binarization. This stage can include, for example, partially transparent to database comparison, manual evaluation, an automatic processing, and the like.

FIG. 33 illustrates method 200 for defect detection using transmissive bright field and transmissive dark field illumination according to an embodiment of the invention.

Method 200 starts by either one of stages 110 or 120. During these stages method 100 tries to evaluate how defects of different types will be detected based upon an actual or a simulated illumination of a target at least partially transparent object by a transmissive dark field illuminator and a transmissive bright field illuminator. Stage 110 and 120 can be viewed as a calibration phase of method 200. It is noted that multiple repetitions of this calibration phase can occur wherein the settings of the transmissive bright field and transmissive dark field illuminators can differ from one iteration to another.

Stages 110 and 120 are followed by stage 230 of determining at least one transmissive bright field illuminator characteristic and at least one transmissive dark field illuminator characteristic so that an image of an at least partially transparent object includes pixels indicative of multiple defect types while information representative of at least one phenomenon to be ignored while information representative of at least one phenomenon to be ignored can be filtered out. The image of the at least partially transparent object is obtained as a result of an illumination of the at least partially transparent object by the transmissive bright field illuminator and by the transmissive dark field illuminator. The at least partially transparent object is at least partially transparent.

Stage 230 is followed by stage 140 of setting the at least one transmissive bright field illuminator characteristic and the at least one transmissive dark field illuminator characteristic according to the determination.

Stage 140 is followed by stage 150 of illuminating the at least partially transparent object by the transmissive dark field illuminator and the transmissive bright field illuminator.

Stage 150 is followed by stage 260 of detecting light that passes through the at least partially transparent object to provide detection signals representative of the image of the electrical circuit.

Stage 260 is followed by stage 170 of processing the detected signals in order to detect defects.

The present invention can be practiced by employing conventional tools, methodology and components. Accordingly, the details of such tools, component and methodology are not set forth herein in detail. In the previous descriptions, numerous specific details are set forth, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

I claim:

1. A method for defect detection using transmissive bright field and transmissive dark field illumination, the method comprises:
   determining a relationship between at least one transmissive bright field illuminator characteristic and at least one transmissive dark field illuminator characteristic in response to at least one characteristic of each defect type out of multiple defect types that should be detected during a defect detection session and in response to at least one phenomenon to be ignored of during the defect detection session;
   setting the at least one transmissive bright field illuminator characteristic and the at least one transmissive dark field illuminator characteristic according to the determination;
   illuminating an at least partially transparent object by the transmissive dark field illuminator and by the transmissive bright field illuminator;
   detecting light that passes through the at least partially transparent object to provide detection signals; and
   processing the detected signals in order to detect defects.

2. The method according to claim 1 wherein the determining is preceded by processing detection signals acquired as a result of an illumination of a target at least partially transparent object by transmissive dark field illumination and by transmissive bright field illumination; wherein the target at least partially transparent object comprises defects that should be detected during the defect detection session and comprises the at least one phenomenon to be ignored of.

3. The method according to claim 1 wherein the determining is preceded by processing detection signals acquired as a result of a simulation of an illumination of a target at least partially transparent object by transmissive dark field illumination and by transmissive bright field illumination; wherein the target at least partially transparent object comprises defects that should be detected during the defect detection session and comprises the at least one phenomenon to be ignored of.

4. The method according to claim 1 comprises determining the relationship between at least one transmissive bright field illuminator characteristic and at least one transmissive dark field illuminator characteristic so that intensities of detection signals obtained as a result of an illumination, by the transmissive dark field illuminator and by the transmissive bright field illuminator, of the multiple defect types that should be detected during the defect detection session are within a narrow range that is substantially narrower than the dynamic range of a detector that generates the detection signals.

5. The method according to claim 1 comprises determining the relationship between at least one transmissive bright field illuminator characteristic and at least one transmissive dark field illuminator characteristic so that intensities of detection signals obtained as a result of an illumination, by the transmissive dark field illuminator and by the transmissive bright field illuminator, of expected defects of different types are substantially the same.

6. The method according to claim 1 comprises determining the relationship between the at least one characteristic of the transmissive dark field illuminator and the at least one characteristic of the transmissive bright field illuminator so that that an image of the at least partially transparent object comprises pixels representative of small defects of the at least partially transparent object and pixels representative of large defects of the at least partially transparent object pixels representative of at least one phenomenon selected out of air bubbles, scratches, dust and contamination have values that can be filtered out during the defect detection session.

7. The method according to claim 1 comprising forming an image of the electrical circuit; and determining the relationship between intensities of the transmissive dark field illuminator and the transmissive bright field illuminator so that that image comprises small defects of the at least partially transparent object and large detects of the at least partially transparent object pixels representative of large detects of the at least partially transparent object pixels representative of at least one phenomenon selected out of air bubbles, scratches, dust and contamination have values that can be filtered out during the defect detection.

8. A defect detection system, the system comprises:
   a transmissive dark field illuminator adapted to illuminate an electrical circuit;
   a transmissive bright field illuminator adapted to illuminate an electrical circuit;
   a detector; adapted to detect light that passes through the at least partially transparent object to provide detection signals; and
   a controller adapted to: (i) determine a relationship between at least one transmissive bright field illuminator characteristic and at least one transmissive dark field illuminator characteristic in response to at least one characteristic of each defect type out of multiple defect types that should be detected during a defect detection session and in response to at least one phenomenon to be ignored of during the defect detection session; (ii) participate in setting the at least one transmissive bright field illuminator characteristic and the at least one transmissive dark field illuminator characteristic according to the determination; and (iii) process the detected signals in order to detect defects.

9. The system according to claim 8 wherein the controller is adapted to process detection signals acquired as a result of an illumination of a target at least partially transparent object by transmissive dark field illumination and by transmissive bright field illumination; wherein the target at least partially transparent object comprises defects that should be detected during the defect detection session and comprises the at least one phenomenon to be ignored of.

10. The system according to claim 8 wherein the controller is adapted to process detection signals acquired as a result of a simulation of an illumination of a target at least partially transparent object by transmissive dark field illumination and by transmissive bright field illumination; wherein the target at least partially transparent object comprises defects that should be detected during the defect detection session and comprises the at least one phenomenon to be ignored of.

11. The system according to claim 8 the controller is adapted to determine the relationship between at least one transmissive bright field illuminator characteristic and at least one transmissive dark field illuminator characteristic so that intensities of detection signals obtained as a result of an illumination, by the transmissive dark field illuminator and by the transmissive bright field illuminator, of expected defects of different types are within a narrow range that is substantially narrower than the dynamic range of the detector.

12. The system according to claim 8 the controller is adapted to determine the relationship between at least one transmissive bright field illuminator characteristic and at least one transmissive dark field illuminator characteristic so that intensities of detection signals obtained as a result of an illumination, by the transmissive dark field illuminator and by the transmissive bright field illuminator, of expected defects of different types are substantially the same.

13. The system according to claim 8 the controller is adapted to determine the relationship between the at least one characteristic of the transmissive dark field illuminator and the at least one characteristic of the transmissive bright field illuminator so that that an image of the at least partially transparent object comprises pixels representative of small defects of the at least partially transparent object and pixels representative of large detects of the at least partially transparent object pixels representative of large detects of the at least partially transparent object wherein pixels representative of at least one phenomenon selected out of air bubbles, scratches, dust and contamination have values that can be filtered out during the defect detection session.

14. The system according to claim 8 adapted to form an image of the electrical circuit; and wherein the controller is adapted to determine the relationship between intensities of the transmissive dark field illuminator and the transmissive bright field illuminator so that that image comprises small defects of the at least partially transparent object and large detects of the at least partially transparent object wherein pixels representative of large detects of the at least partially transparent object pixels representative of at least one phenomenon selected out of air bubbles, scratches, dust and contamination have values that can be filtered out during the defect detection session.

15. A method for defect detection using transmissive bright field and transmissive dark field illumination, the method comprises:
determining at least one transmissive bright field illuminator characteristic and at least one transmissive dark field illuminator characteristic so that an image of an at least partially transparent object comprises pixels indicative of multiple defect types while information representative of at least one phenomenon to be ignored while information representative of at least one phenomenon to be ignored can be filtered out; wherein the image of the at least partially transparent object is obtained as a result of an illumination of the at least partially transparent object by the transmissive bright field illuminator and by the transmissive dark field illuminator comprises pixels and wherein the at least partially transparent object is at least partially transparent;
setting the at least one transmissive bright field illuminator characteristic and the at least one transmissive dark field illuminator characteristic according to the determination;
illuminating an at least partially transparent object by the transmissive dark field illuminator and the transmissive bright field illuminator;
detecting light that passes through the at least partially transparent object to provide detection signals representative of the image of the electrical circuit; and
processing the detected signals in order to detect defects.

16. The method according to claim 15 wherein the determining is preceded by processing detection signals acquired as a result of an illumination of a target at least partially transparent object by transmissive dark field illumination and by transmissive bright field illumination; wherein the target at least partially transparent object comprises defects of multiple types that should be detected during the defect detection session and comprises the at least one phenomenon to be ignored of.

17. The method according to claim 15 wherein the determining is preceded by processing detection signals acquired as a result of a simulation of an illumination of a target at least partially transparent object by transmissive dark field illumination and by transmissive bright field illumination; wherein the target at least partially transparent object comprises defects of multiple types that should be detected during the defect detection session and comprises the at least one phenomenon to be ignored of.

18. The method according to claim 15 comprises determining the at least one transmissive bright field illuminator characteristic and the at least one transmissive dark field illuminator characteristic so intensities of pixels indicative of defects of multiple types are within a narrow range that is substantially narrower than a dynamic range of a detector that generates the detection signals.

19. The method according to claim 15 comprises determining the at least one transmissive bright field illuminator characteristic and the at least one transmissive dark field illuminator characteristic so intensities of pixels indicative of defects of multiple types are substantially the same.

20. The method according to claim 15 comprises determining the at least one characteristic of the transmissive dark field illuminator and the at least one characteristic of the transmissive bright field illuminator so that that the image of the at least partially transparent object comprises pixels representative of small defects of the at least partially transparent object and pixels representative of large detects of the at least partially transparent object wherein pixels representative of large detects of the at least partially transparent object pixels representative of at least one phenomenon selected out of air bubbles, scratches, dust and contamination have values that can be filtered out during the defect detection session.

21. A system for defect detection, the system comprises:
a transmissive dark field illuminator adapted to illuminate an at least partially transparent object that is at least partially transparent;
a transmissive bright field illuminator adapted to illuminate the electrical circuit;
a detector; adapted to detect light that passes through the at least partially transparent object to provide detection signals representative of an image of the electrical circuit; and
a controller adapted to: (i) determine at least one transmissive bright field illuminator characteristic and at least one transmissive dark field illuminator characteristic so that the image of the at least partially transparent object comprises pixels indicative of each defect type out of multiple defect types while information representative of at least one phenomenon to be ignored while information representative of at least one phenomenon to be ignored can be filtered out; (ii) participate in setting the at least one transmissive bright field illuminator characteristic and the at least one transmissive dark field illuminator characteristic according to the determination; and (iii) process the detected signals in order to detect defects.

22. The system according to claim 21 wherein the controller is adapted to process detection signals acquired as a result of an illumination of a target at least partially transparent object by transmissive dark field illumination and by transmissive bright field illumination; wherein the target at least partially transparent object comprises defects of multiple types that should be detected during the defect detection session and comprises the at least one phenomenon to be ignored of.

23. The system according to claim 21 wherein the controller is adapted to determine the at least one transmissive bright field illuminator characteristic and the at least one transmissive dark field illuminator characteristic so intensities of pixels indicative of defects of multiple types are within a narrow range that is substantially narrower than a dynamic range of a detector that generates the detection signals.

24. The method according to claim 21 comprises wherein the controller is adapted to determine the at least one transmissive bright field illuminator characteristic and the at least one transmissive dark field illuminator characteristic so intensities of pixels indicative of defects of multiple types are substantially the same.

25. The system according to claim 21 wherein the controller is adapted to determine the at least one characteristic of the transmissive dark field illuminator and the at least one characteristic of the transmissive bright field illuminator so that that the image of the at least partially transparent object comprises pixels representative of small defects of the at least partially transparent object and pixels representative of large detects of the at least partially transparent object wherein pixels representative of large detects of the at least partially transparent object pixels representative of at least one phenomenon selected out of air bubbles, scratches, dust and contamination have values that can be filtered out during the defect detection session.

* * * * *